US012402778B2

(12) United States Patent
Harrah et al.

(10) Patent No.: US 12,402,778 B2
(45) Date of Patent: Sep. 2, 2025

(54) MEDICAL DEVICE AND METHODS OF USE

(71) Applicant: Boston Scientific Scimed, Inc., Maple Grove, MN (US)

(72) Inventors: Timothy P. Harrah, Cambridge, MA (US); Christopher L. Oskin, Grafton, MA (US); Derrick Lenz, Pompton Plains, NJ (US); Arpita Banerjee, Bangalore (IN); Sandesh Gavade, Bangalore (IN); Abhijit Takale, Pune (IN); Pavan Misra, Bangalore (IN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 96 days.

(21) Appl. No.: 18/350,383

(22) Filed: Jul. 11, 2023

(65) Prior Publication Data
US 2023/0346202 A1  Nov. 2, 2023

Related U.S. Application Data

(60) Continuation of application No. 16/679,406, filed on Nov. 11, 2019, now Pat. No. 11,737,650, which is a
(Continued)

(51) Int. Cl.
*A61B 1/00* (2006.01)
*A61B 1/015* (2006.01)
(Continued)

(52) U.S. Cl.
CPC ...... *A61B 1/00094* (2013.01); *A61B 1/00135* (2013.01); *A61B 1/015* (2013.01);
(Continued)

(58) Field of Classification Search
CPC ....... A61B 18/24; A61B 18/245; A61B 18/26; A61B 18/263; A61B 2018/266;
(Continued)

(56) References Cited

U.S. PATENT DOCUMENTS

| 4,487,600 A | 12/1984 | Brownlie et al. |
| 4,725,264 A | 2/1988 | Glassman |

(Continued)

FOREIGN PATENT DOCUMENTS

| CN | 101044971 A | 10/2007 |
| CN | 103379849 A | 10/2013 |
| WO | 2015/147159 A1 | 10/2015 |

OTHER PUBLICATIONS

International Search Report and Written Opinion for International Application No. PCT/US2017/014943, mailed Apr. 3, 2017 (12 pages).
(Continued)

*Primary Examiner* — Ahmed M Farah
(74) *Attorney, Agent, or Firm* — Bookoff McAndrews PLLC

(57) ABSTRACT

The present disclosure is directed to a medical device. Systems and methods are provided for utilizing a laser to break a kidney stones into smaller fragments and/or dust, and removing particles, stone fragments and/or stone dust from a patient. The medical device may include a delivery device including a tube, and an elongate member having a distal end, a proximal end, and a lumen extending between the proximal end and the distal end, wherein the elongate member is configured to move axially relative to the tube and apply suction through the distal end.

20 Claims, 7 Drawing Sheets

Related U.S. Application Data division of application No. 15/415,604, filed on Jan. 25, 2017, now Pat. No. 10,499,936.

(60) Provisional application No. 62/288,734, filed on Jan. 29, 2016.

(51) Int. Cl.

| | | |
|---|---|---|
| *A61B 1/307* | (2006.01) | |
| *A61B 17/22* | (2006.01) | |
| *A61B 17/30* | (2006.01) | |
| *A61B 18/24* | (2006.01) | |
| *A61B 18/26* | (2006.01) | |
| *A61M 1/00* | (2006.01) | |
| *A61B 18/00* | (2006.01) | |
| *A61B 90/00* | (2016.01) | |
| *A61B 90/30* | (2016.01) | |

(52) U.S. Cl.
CPC .............. *A61B 1/307* (2013.01); *A61B 17/22* (2013.01); *A61B 17/30* (2013.01); *A61B 18/245* (2013.01); *A61B 18/26* (2013.01); *A61M 1/84* (2021.05); *A61B 2017/306* (2013.01); *A61B 2018/00511* (2013.01); *A61B 2018/00982* (2013.01); *A61B 90/30* (2016.02); *A61B 90/361* (2016.02); *A61M 1/85* (2021.05); *A61M 2205/106* (2013.01); *A61M 2210/1082* (2013.01)

(58) Field of Classification Search
CPC ........... A61B 2018/00505; A61B 2018/00511; A61B 2018/00517; A61B 17/30; A61B 2017/306; A61B 17/32; A61B 2017/320016; A61B 2017/32007; A61B 1/00096; A61B 1/0015; A61B 1/307
USPC .................................................. 606/2.5, 205
See application file for complete search history.

(56) References Cited

U.S. PATENT DOCUMENTS

| | | | |
|---|---|---|---|
| 5,298,026 A * | 3/1994 | Chang | ................. A61N 5/0601 606/15 |
| 5,312,399 A | 5/1994 | Hakky et al. | |
| 5,324,282 A | 6/1994 | Dodick | |
| 5,476,450 A | 12/1995 | Ruggio | |
| 5,599,299 A | 2/1997 | Weaver et al. | |
| 5,718,709 A | 2/1998 | Considine et al. | |
| 6,461,349 B1 | 10/2002 | Elbrecht et al. | |
| 7,104,983 B2 | 9/2006 | Grasso et al. | |
| 8,852,084 B2 | 10/2014 | Crank | |
| 9,393,033 B2 * | 7/2016 | Zerfas | ................... A61B 90/30 |
| 10,004,560 B2 | 6/2018 | Zerfas et al. | |
| 2002/0072651 A1 | 6/2002 | Vilos | |
| 2002/0161358 A1 | 10/2002 | Liu et al. | |
| 2011/0202039 A1 | 8/2011 | Schaaf | |
| 2011/0224489 A1 | 9/2011 | Deal et al. | |
| 2013/0131445 A1 | 5/2013 | Zerfas et al. | |
| 2013/0261639 A1 | 10/2013 | Schaeffer et al. | |
| 2014/0005490 A1 | 1/2014 | Vayser | |
| 2014/0024901 A1 | 1/2014 | Vayser et al. | |
| 2015/0335813 A1 | 11/2015 | Qian | |
| 2016/0120557 A1 | 5/2016 | Goddard et al. | |

OTHER PUBLICATIONS

European Search Report in Application No. 231728895.7, dated Aug. 11, 2023 (8 pages).

\* cited by examiner

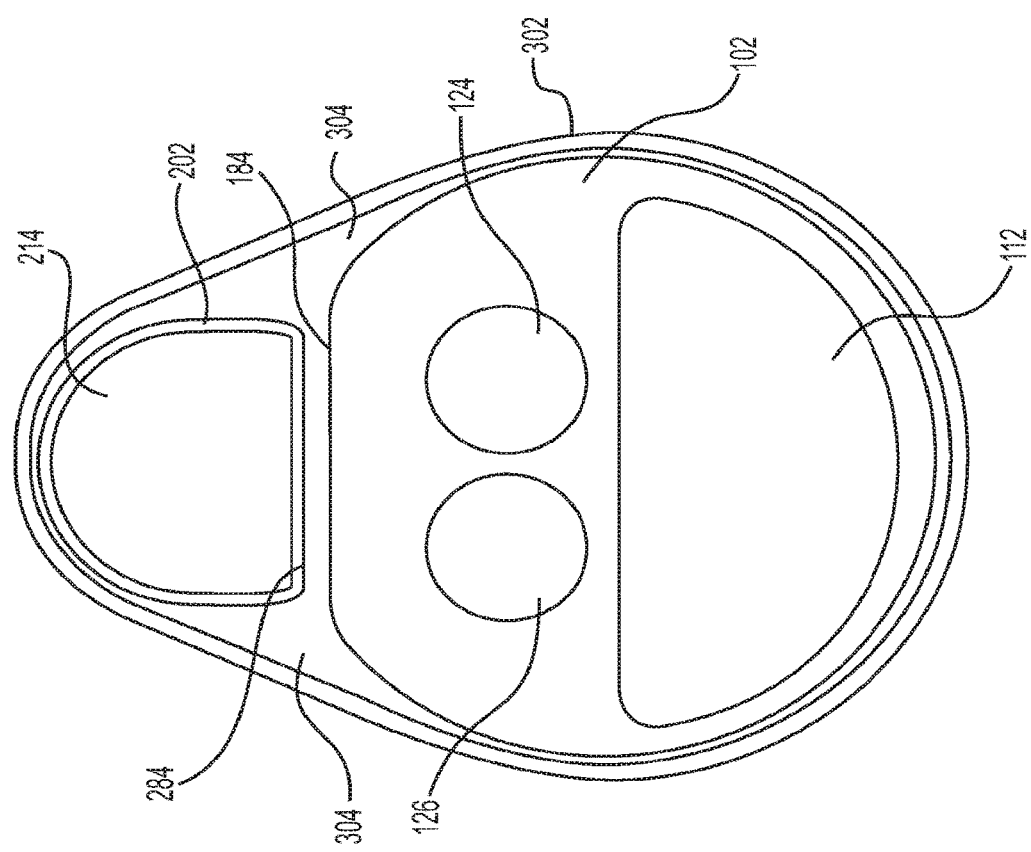

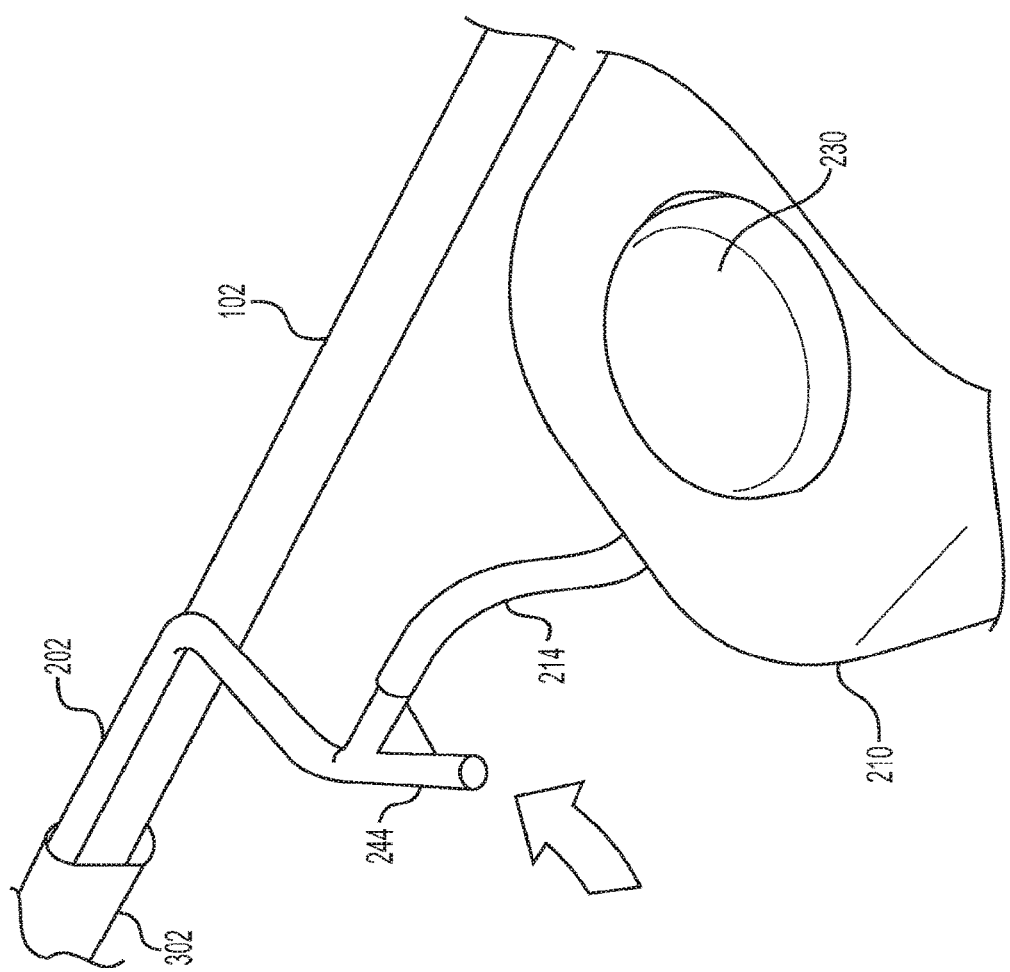

MEDICAL DEVICE AND METHODS OF USE

CROSS-REFERENCE TO RELATED APPLICATIONS

This patent application is a continuation of U.S. application Ser. No. 16/679,406, filed Nov. 11, 2019, which is a divisional of U.S. application Ser. No. 15/415,604, filed Jan. 25, 2017, now U.S. Pat. No. 10,499,936, which claims the benefit of priority under 35 U.S.C. § 119 to U.S. Provisional Patent Application No. 62/288,734, filed Jan. 29, 2016, each of which is herein incorporated by reference in its entirety.

TECHNICAL FIELD

The present disclosure relates generally to medical devices. More particularly, the disclosure relates to medical devices used, for example, in breaking objects into smaller particles, and removing the resulting particles from a patient. The disclosure also relates to methods of using such devices.

BACKGROUND

The incidence of hospitalization for the removal of urinary calculi, commonly referred to as kidney stones, has been estimated at 200,000 cases per year. A vast majority of these patients pass their stones spontaneously; however, in the remainder, the kidney stone(s) become impacted in the ureter, a muscle tube joining the kidney to the bladder. An impacted kidney stone is a source of intense pain and bleeding, a source of infection and, if a stone completely blocks the flow of urine for any extended length of time, can cause the loss of a kidney.

Recently, various methods have been utilized to break the stone into smaller fragments. One such method is stone dusting. Stone dusting is used by some urologists to fragment and evacuate stones from a kidney and is often performed by a ureteroscope. Intense light energy from a laser within the ureteroscope breaks the stone into increasingly smaller pieces. However, in some cases, the stone and/or the stone fragments may be pushed away from the ureteroscope by the laser, thus making it impossible to continue to break the stone or stone fragments into smaller fragments without repositioning the ureteroscope. The disclosure addresses the above-mentioned process and other problems in the art.

Further, rather than breaking up the stone into chunks, which are removed by baskets, dusting generates very small fragments that are capable of being passed naturally. However, in some cases, these small stone fragments may not pass naturally. For example, the stone fragments may collect in an area of the kidney where they are less likely to flow out naturally, such as the lower calyx of the kidney. In theory, any of these small stone fragments that do not evacuate through natural urine flow, could be a seed for new stone growth. Thus, the application of suction may be employed to remove the stone dust. Breaking up a stone and providing suction requires a working channel with a sufficient internal cross-sectional area to receive a laser fiber and a lumen with sufficient internal cross-sectional area to allow stone fragments and/or dust to pass through without clogging. The combined cross-sectional areas of these two elements may make a device too large to reach the target kidney stone. For example, the kidney stone may be within the kidney, or, specifically, within the lower calyx of the kidney. Often, the space within the kidney and/or lower calyx of the kidney is more limited than the space within the ureter and this space may not be large enough to accommodate both a working channel for a laser fiber and a lumen for applying suction. The disclosure addresses the above-mentioned process and other problems in the art.

SUMMARY OF THE DISCLOSURE

Aspects of the present disclosure provide device and methods for breaking an object into smaller particles and removing said particles from portions of the human body.

It is to be understood that both the foregoing general description and the following detailed description are exemplary and explanatory only and are not restrictive.

In one example, a medical device may include a delivery device including a tube, and an elongate member having a distal end, a proximal end, and a lumen extending between the proximal end and the distal end, wherein the elongate member is configured to move axially relative to the tube and apply suction through the distal end.

Examples of the medical device may additionally and/or alternatively include one or more other features. Features of the various examples described in the following may be combined unless explicitly stated to the contrary. For example, the proximal end of the elongate member may be forked. The proximal end of the elongate member may be connected to a control system. The control system may control the vacuum source. The proximal end of the elongate member may be in fluid communication with a vacuum source. The medical device may include a sleeve, wherein the sleeve may be configured to receive the tube and the elongate member simultaneously. The delivery device may be one of ureteroscope, sheath, catheter, or endoscope. The medical device may include a laser fiber connected to the tube. The lumen of the elongate member may be substantially D-shaped. The tube may include an illumination device. The tube may include an imaging device. The tube may have a first engaging surface, and the elongate member may have a second engaging surface, and the first engaging surface may be substantially complementary of the second engaging surface. The elongate member may be in fluid communication with a fluid source. The lumen of the elongate member may have an inner diameter of approximately 1 mm to approximately 3.5 mm. The elongate member may be at least partially controlled by a control system and the tube may be at least partially controlled by a handle.

In another example, a method operating a medical device may include positioning a distal end of an elongate member of the medical device at a target area, applying suction through a lumen of the elongate member to seal an object to the distal end of the elongate member, and moving the distal end of the elongate member to move the object sealed to the distal end of the elongate member.

Examples of the method of operating the medical device may additionally and/or alternatively include one or more other features. For example, prior to positioning the distal end of the elongate member of the medical device at the target area, the method may include positioning the distal end of the elongate member proximal to the target area, and supplying dye through the lumen of the elongate member to the distal end of the elongate member. The method may include moving the object proximate to a tube, disposing a laser fiber within the tube, and initiating the laser.

In another example, a method operating a medical device may include positioning a distal end of an elongate member of the medical device distal to a distal end of a tube of the medical device, applying suction through a lumen of the elongate member to seal a kidney stone to the distal end of the elongate member, and moving the distal end of the elongate member to move the kidney stone sealed to the distal end of the elongate member proximally toward the distal end of the tube.

Examples of the method of operating the medical device may additionally and/or alternatively include one or more other features. For example, the method may include disposing a laser fiber within the tube, and initiating the laser.

BRIEF DESCRIPTION OF THE DRAWINGS

The accompanying drawings, which are incorporated in and constitute a part of this specification, illustrate various examples and together with the description, serve to explain the principles of the disclosure.

FIG. 3A illustrates an exemplary cross-section of the medical device taken at 3-3 of FIG. 1;

FIG. 4 illustrates an exemplary connection between a proximal end of the elongate member and the control system of FIG. 1;

DETAILED DESCRIPTION

Reference is now made in detail to examples of the present disclosure, examples of which are illustrated in the accompanying drawings. Wherever possible, the same reference numbers will be used throughout the drawings to refer to the same or like parts. The term "distal" refers to a position farther away from a user end of the device. The term "proximal" refers a position closer to the user end of the device. As used herein, the terms "approximately" and "substantially" indicate a range of values within +/−5% of a stated value.

Overview

Aspects of the present disclosure relate to systems and methods for breaking kidney stones into smaller particles and removing those particles from a target area of a patient's body. The medical device described herein may work by securing an elongate member for suction to an outer surface of a tube of a delivery device. A distal end of the tube and a distal end of the elongate member may be positioned within a ureter of a patient. In some examples, radiopaque dye may be injected into the target area, e.g., the kidney, from a lumen of the elongate member. Then, the elongate member may be extended distally to a retrieval position in which the distal end of the elongate member is positioned within the target area, e.g., the lower calyx of the kidney, and/or proximate the target kidney stone. Suction may be applied through the elongate member, pulling the stone toward a distal opening of the elongate member until the stone contacts and forms a seal with the distal opening of the elongate member. The formed seal secures the kidney stone to the distal opening of the elongate member. With the stone secured to the elongate member, the elongate member may be retracted or pulled proximally toward the distal end of the tube until the elongate member is in the operating position, e.g., the secured stone is proximate a distal opening of the tube. At this point, a laser fiber, disposed within the tube, may be used to break up kidney stones into particles. It should be noted that the stone may be broken into particles in any way known in the art, including the application of ultrasound and/or sound waves on the stone. Once the stone is broken into particles that are smaller than the distal opening the elongate member, the seal may be broken and/or particles may be suctioned into the lumen of the elongate member. These particles may be vacuumed through the elongate member and out of the patient's body.

Detailed Examples

Figure 1:
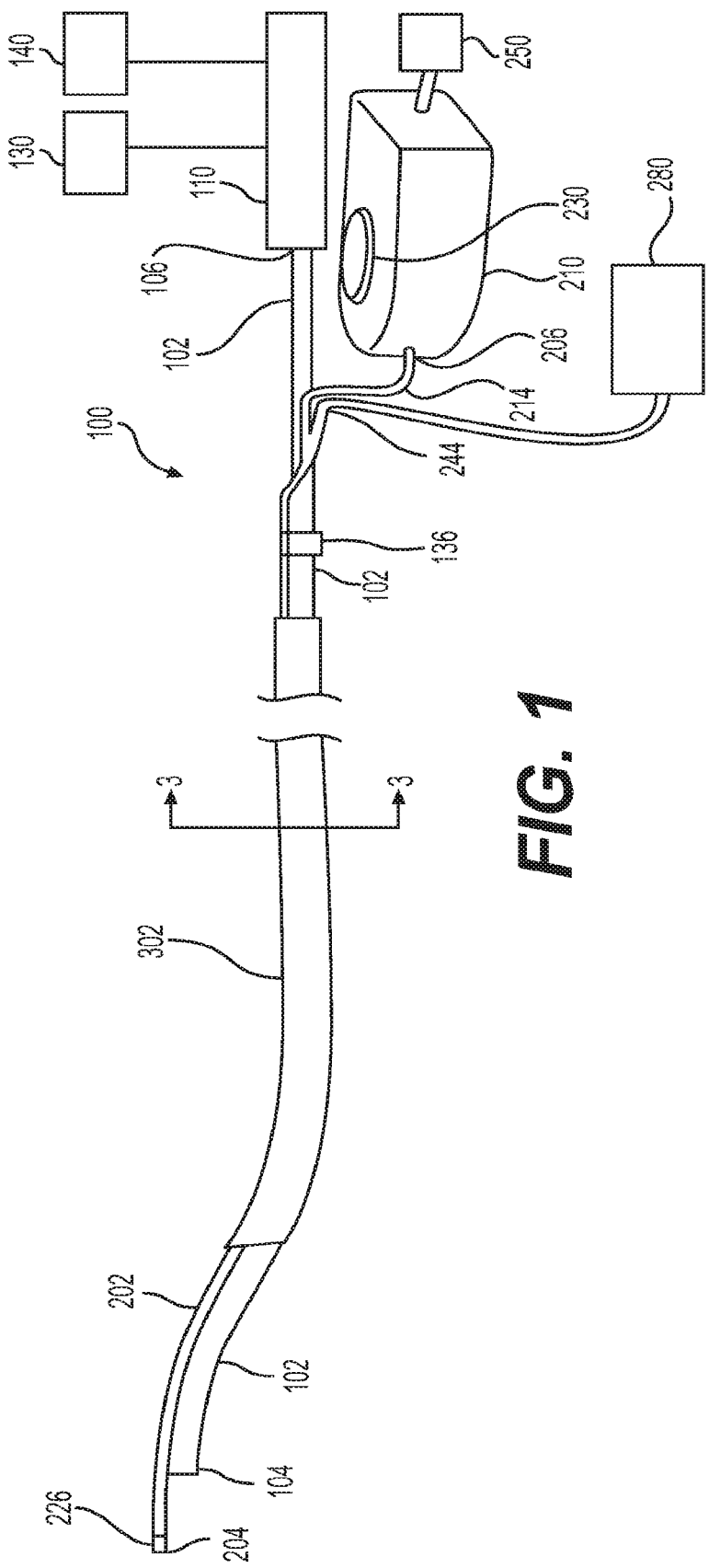
FIG. 1 illustrates an exemplary medical device, including a tube, an elongate member, a handle portion, a control system, and a sleeve.

FIG. 1 illustrates medical device 100 for removing stones from a patient's body. Medical device 100 may include a retrieval system. The retrieval system may include elongate member 202 and control system 210. Elongate member 202 may be a hollow, flexible, elongate tube having a distal end 204 and a proximal end 206 and at least one lumen (e.g., lumen 214 of FIGS. 2A-B) extending therebetween. Proximal end 206 of elongate member 202 may be coupled to control system 210, vacuum source 250, and/or fluid source 280. As shown in FIG. 1, medical device 100 may include a delivery device. The delivery device may be, for example, any traditional delivery device, including a ureteroscope, sheath, catheter, endoscope, etc. The delivery device may include a tube 102 and a handle portion 110. Tube 102 may be a hollow, flexible, elongate tube having a distal end 104 and a proximal end 106 and at least one lumen (e.g., lumen 112 of FIGS. 2A-B) extending therebetween. Proximal end 106 of tube 102 may be coupled to handle portion 110. The handle portion 110 and/or the proximal end 106 of tube 102 may be attached to a laser control 130 and/or a fluid supply assembly 140. In some examples, medical device 100 may include a sleeve 302 and fastener 136. Sleeve 302 and fastener 136 may be any mechanism known in the art for allowing elongate member 202 (and/or the entirety of the retrieval device) to move axially relative to tube 102 and prevent radial movement of elongate member 202 relative to tube 102.

Depending upon the particular implementation and intended use, the length of tube 102, elongate member 202, and/or sleeve 302 may vary. In the example shown in FIG. 1, sleeve 302 may be shorter in length than tube 102 and elongate member 202. Depending upon the particular implementation and intended use, tube 102, elongate member 202, and/or sleeve 302 can be rigid along its entire length, flexible along a portion of its length, or configured for flexure at only certain specified locations. In one example, tube 102, elongate member 202, and/or sleeve 302 may be flexible, adapted for flexible steering within bodily lumens, as understood in the art. For example, tube 102 can include a steering system (not shown) to move at least a portion (e.g., distal end 104) up/down and/or side-to-side. Additional degrees of freedom, provided for example via rotation, translational movement of tube 102, or additional articulation of bending sections, may also be implemented. Examples of such steering systems may include at least one of or more of pulleys, control wires, gearing, and electrical actuators.

Tube 102, elongate member 202, and/or sleeve 302 may be formed of any suitable material having sufficient flexibility to traverse body cavities and tracts. In general, tube 102, elongate member 202, and/or sleeve 302 may be made of any suitable material that is compatible with living tissue or a living system. That is, tube 102, elongate member 202, and/or sleeve 302 may be non-toxic or non-injurious, and it should not cause immunological reaction or rejection. In some examples, tube 102, elongate member 202, and/or sleeve 302 may be made of polymeric elastomers, rubber tubing, and/or medically approved polyvinylchloride tubing. Polymeric elastomers may be, for example, EVA (Ethylene vinyl acetate), silicone, polyurethane, and/or C-Flex.

Further, tube 102, elongate member 202, and/or sleeve 302 may include any suitable coating and/or covering. For example, the outer surface may include a layer of lubricous material to facilitate insertion through a body lumen or through sleeve 302. Further, tube 102, elongate member 202, and/or sleeve 302 may be coated with a biocompatible material such as Teflon. To inhibit bacterial growth in the body cavity, tube 102, elongate member 202, and/or sleeve 302 may be coated with an antibacterial coating. Further, an anti-inflammatory substance may also be applied to the outer surface of the tube 102, elongate member 202, and/or sleeve 302, if required.

Tube 102, elongate member 202, and/or sleeve 302 may be designed to impose minimum risk to the surrounding tissues while in use. To this end, one or more portions of tube 102, elongate member 202, and/or sleeve 302 may include atraumatic geometrical structures, such as rounded or beveled terminal ends or faces (e.g., distal end 104 of tube 102), to reduce trauma and irritation to surrounding tissues.

I. Sleeve

Sleeve 302 may be hollow and configured to slidably receive tube 102 and elongate member 202 simultaneously. Tube 102 may be circular, ovoidal, irregular, and/or any shape suitable to enter a body and/or receive tube 102 and elongate member 202. In some examples, a lumen running through sleeve 302 may be shaped to accommodate the size and shape of tube 102 and elongate member 202. In other examples, the lumen may be substantially circular and sleeve 302 may be made of elastic material to stretch to accommodate the size and shape of the combination of tube 102 and elongate member 202. A lumen extending through sleeve 302 may include any suitable coating. For example, the lumen may include a layer of lubricous material, for example, to facilitate insertion of tube 102 and elongate member 202.

II. Delivery Device

As previously described, medical device 100 may include a delivery device. The delivery device may be, for example, any delivery device known in the art, including ureteroscope, sheath, catheter, endoscope, etc. The delivery device may include a tube 102 and a handle portion 110.

A. Handle Portion

Handle portion 110 can be attached to proximal end 106 of tube 102 by, for example, welding, a locking configuration, use of an adhesive, or integrally forming with tube 102. The handle portion 110 may include a plurality of ports. For example, a first port may supply to distal end 104 of tube 102 a laser fiber (e.g., laser fiber 120) coupled to laser control (e.g., laser control 130). In some examples, a second port may place lumen 112 in fluid communication with a fluid supply assembly (e.g., fluid supply assembly 140). Additional ports and lumens may be provided for supplying and/or controlling an illumination device and/or an imaging device located at or near distal end 104 of tube 102. The handle portion 110 may include an actuating mechanism (not shown) to actuate one or more medical devices that may be located at the distal end 104 of tube 102. For example, handle portion 110 may include an actuating mechanism to power on or off the laser, the illumination device, and/or the imaging device.

B. The Tube

Tube 102 may be circular, ovoidal, irregular, and/or any shape suitable to enter a body. Further, tube 102 may have a uniform shape along its length, or may having a varying shape, such as a taper at the distal end to facilitate insertion within the body. In some embodiments of the present disclosure, the distal end 104 of tube 102 includes visualization devices such as a camera and/or a light source. These devices may attach to the distal end 104 using known coupling mechanisms. Alternatively, the visualization devices may be detachably introduced into tube 102 through lumen 112 (or a separate lumen, e.g., lumen 124 or 126 of FIGS. 2A-B) when required.

Lumen 112 may be defined by an elongate hollow lumen that extends between proximal end 106 and distal end 104 of tube 102. Lumen 112 may be any size, shape, and/or in any configuration within tube 102. Exemplary cross-sections of tube 102 and lumen 112 will be described in further detail below with respect to FIGS. 3A and 3B.

III. Retrieval System

As previously described, medical device 100 may include a retrieval system. The retrieval system may include elongate member 202 and control system 210.

A. The Elongate Member

Elongate member 202 may be circular, ovoidal, irregular, and/or any shape suitable to enter a body and/or sleeve 302. Further, elongate member 202 may have a uniform shape along its length, or may having a varying shape, such as a taper at the distal end to facilitate insertion within the body. In some embodiments of the present disclosure, the distal end 204 of elongate member 202 includes reinforced section 226. The walls of reinforced section 226 may be thicker than the remainder of elongate member 202. This may prevent distortion of the reinforced section 226 when a stone is vacuumed and held against a distal opening/distal end 204 (as described in further detail below with respect to FIGS. 5A-C).

Lumen 214 may be defined by an elongate hollow lumen that extends between proximal end 206 and distal end 204 of elongate member 202. Lumen 214 may be any size, shape, and/or in any configuration within elongate member 202. For example, the inner diameter of lumen 214 may be approximately 1 mm to approximately 3.5 mm, approximately 1.5 mm to approximately 3 mm, or approximately 2 mm to approximately 3 mm. Exemplary cross-sections of elongate member 202 and lumen 214 will be described in further detail below with respect to FIGS. 3A and 3B.

In some examples, elongate member 202 may act as a guidewire to guide attached tube 202. For example, elongate member 202 may be inserted into the body before the insertion of tube 102, and tube 102 may be tracked along an outer surface (e.g., engaging surface 284) of elongate member 202 in order to position tube 102 within the body. It should be noted that any of lumens 112 or 214 may additionally or alternatively be configured to receive a guidewire. In some embodiments, lumen 214 may receive a guidewire to facilitate positioning elongate member 202 in the body.

To effectively maneuver the elongate member 202 within a body cavity and, for example, position distal end 204 proximate of a kidney stone within a lower calyx of a kidney, an operator may need to know the exact location of the elongate member 202 in the body. To this end, one or more portions of elongate member 202 may be made of radiopaque, such as by inclusion of barium sulfate in plastic material or inclusion of one or more metal portions, which provide sufficient radiopacity. In some examples, elongate member 202 may have a radiopaque coating. Additionally or alternatively, distal end 204 of elongate member 202 may include radiopaque or sonoreflective markers (not shown). These markings facilitate detection of a position and/or orientation of elongate member 202 within a patient's body, and an operator, with the aid of suitable imaging equipment, may track the path followed by elongate member 202. This may help the operator avoid potential damage to sensitive tissues. By using fluoroscopic guidance, elongate member 202 may be located without the visualization devices within tube 102 and, therefore, move independently of and/or not within the field of view of these visualization devices. Further, with such guidance, the space within elongate member 202 that would be needed for direct visualization (e.g., an imaging apparatus) may instead be used to maximize the size of the lumen and/or the flow rate of the suction.

Figure 2A:
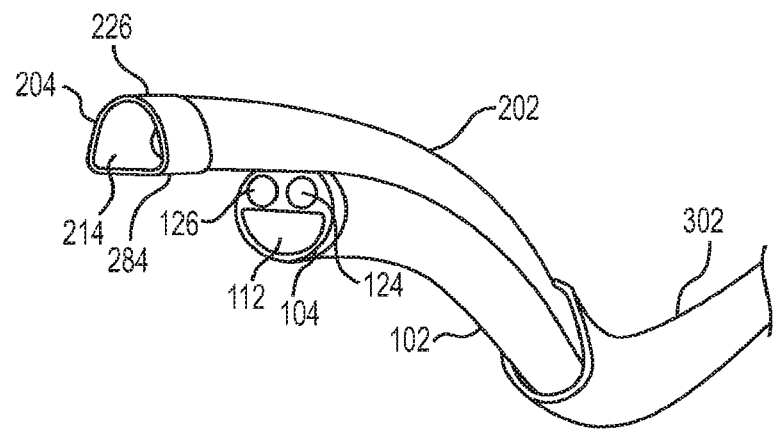
FIG. 2A illustrates an exemplary distal end of the medical device of FIG. 1 with the elongate member in a retrieval position.
Figure 2B:
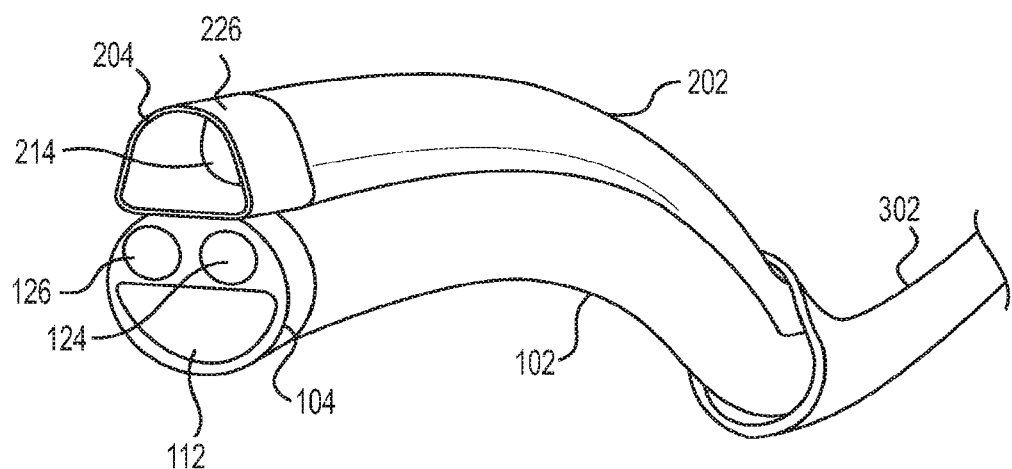
FIG. 2B illustrates an exemplary distal end of the medical device of FIG. 1 with the elongate member in an operating position.

FIGS. 2A-B illustrate exemplary distal ends of medical device 100 with elongate member 202 in a retrieval position and an operating position, respectively. As shown in FIG. 2A, in a retrieval position, distal end 204 of elongate member 202 may be distal of the distal end 104 of tube 102. In an operating position, as shown in FIG. 2B, distal end 204 of elongate member 202 may be closer to and/or flush with the distal end 104 of tube 102.

FIG. 3A illustrates a cross-sectional view of an exemplary medical device 100. This view may, for example, be at line 3-3 of FIG. 1. As shown, tube 102 may include a lumen 112, illumination device 126, imaging apparatus 124, and/or engaging surface 184. Lumen 112 may be semi-circular in shape. Lumen 112, however, may have any cross-sectional size and/or shape. In the example shown in FIG. 3A, engaging surface 184 may be substantially planar. Engaging surface 184 is not limited thereto and may have shape, including any shape that is substantially complementary with an engaging surface of an elongate member (e.g., engaging surface 284 of tube 202). For example, as shown in FIG. 3A, elongate member 202 has a substantially planar engaging surface 284. Lumen 214 of elongate member 202 may be substantially D-shaped, however, lumen 214 is not limited thereto and may have any cross-sectional size and/or shape. FIG. 3A shows a space between engaging surface 284 of elongate member 202 and engaging surface 184 of tube 102. In some examples, however, gravity may pull and/or sleeve 302 may push engaging surface 284 of elongate member 202 to contact engaging surface 184 of tube 102. Sleeve 302 should be configured to avoid so much friction as to restrict axial movement of elongate member 202 relative to tube 102. Spaces 304 are spaces between an interior wall of sleeve 302 and the outer surfaces of elongate member 202 and/or tube 102. In some examples, these spaces may be minimized, for example, if sleeve 302 is made of an elastic material configured to "hug" on the outer surfaces of elongate member 202 and/or tube 102.

Figure 3B:
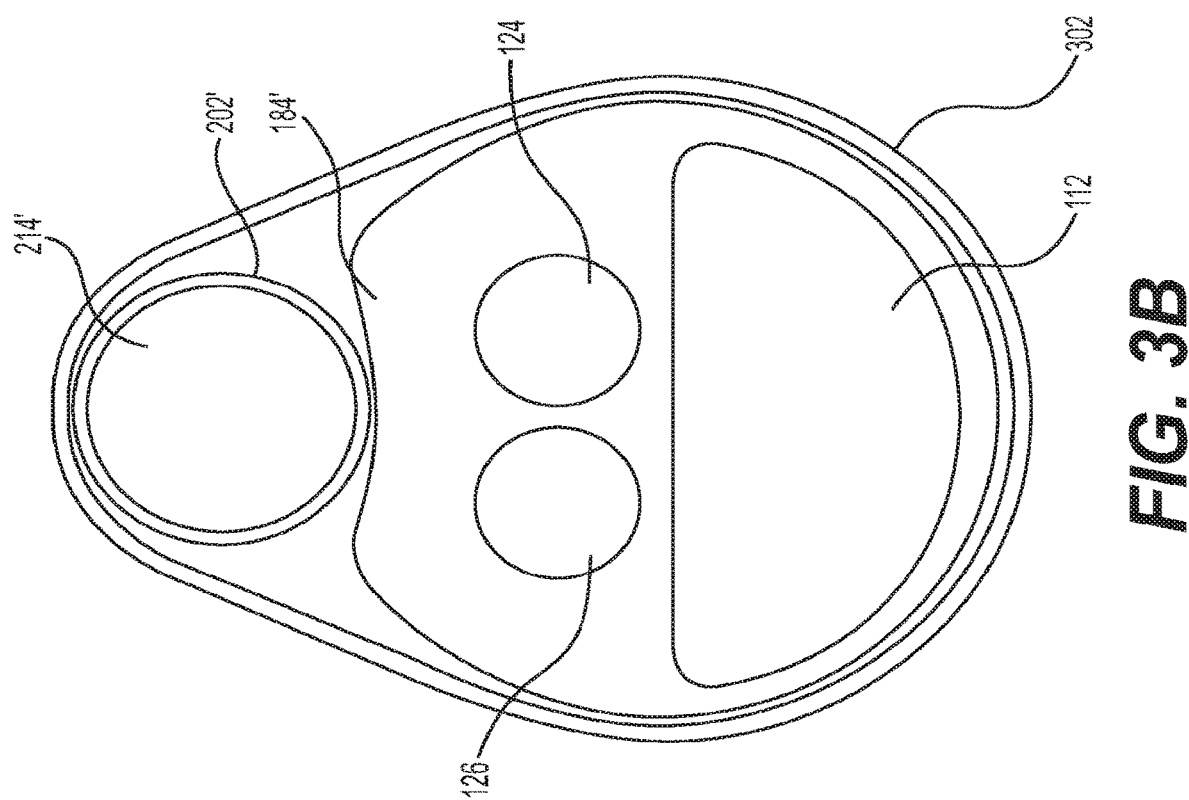
FIG. 3B illustrates an alternative exemplary cross-section of the medical device taken at 3-3 of FIG. 1.

FIG. 3B illustrates a cross-sectional view of an alternative exemplary medical device 100. This view may, for example, be at line 3-3 of FIG. 1. As shown, the cross-sectional area of elongate member 202' and lumen 214' of elongate member 202' are substantially circular. Tube 102 includes a lumen 112, illumination device 126, imaging apparatus 124, and/or engaging surface 184'. Engaging surface 184' is substantially concave and may be substantially complementary to an outer surface of elongate member 202'.

It should be noted that in some examples, elongate member 202 and/or elongate member 202' may be configured to engage (and/or slide across) an outer surface of a conventional or substantially circular delivery device. In such examples, engaging surface 284 and/or 284' may be concave and/or be complementary with the outer surface of a substantially circular delivery device.

B. Control System

FIG. 4 is an enlarged exemplary view of proximal end 206 of elongate member 202 and control system 210. Distal of proximal end 206, elongate member 202 may fork, for example, into first end 214 and second end 244. First end 244 of elongate member 202 may be open and configured to attach to, for example any fluid source known in the art, e.g., a fluid source 280 of FIG. 1. For example, dye or, more specifically, radiopaque dye may be within fluid source 280.

Second end 214 of elongate member 202 may attach to control system 210 by, for example, a locking configuration, use of an adhesive, or integrally forming with elongate member 202. Control system 210 may allow an operator to control operation of the retrieval system. For example, as described in further detail below, control system 210 may include the ability to control steering of elongate member 202, introduce dye into elongate member 202, and/or apply suction through elongate member 202. In some examples, control system 210 may include or be in fluid communication with a vacuum source, e.g., vacuum source 250 of FIG. 1. A vacuum source may include a house vacuum, vacuum pump, compressor unit, etc. Control system 210 may include any input devices known in the art, including buttons, switches, keyboards, dials, touchscreens, etc. Input device 230 may, for example, be an on-off button to turn on or off the vacuum source and either apply or cease application of suction from distal end 204 of elongate member 202. Input device 230 may be a dial for adjusting the flow rate of this suction.

IV. Insertion and Operation of the Medical Device

Figure 5A:
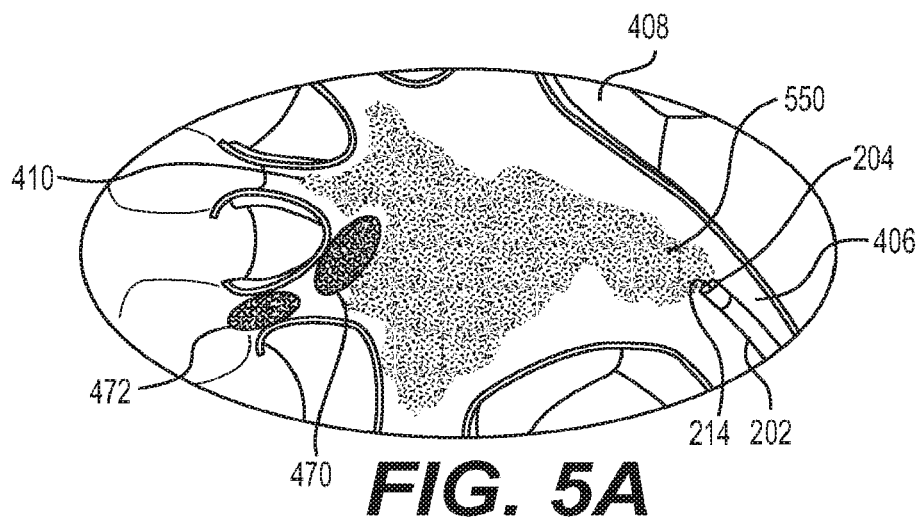
FIGS. 5A-C illustrates an exemplary method of operation of the medical device of FIG. 1.
Figure 5B:
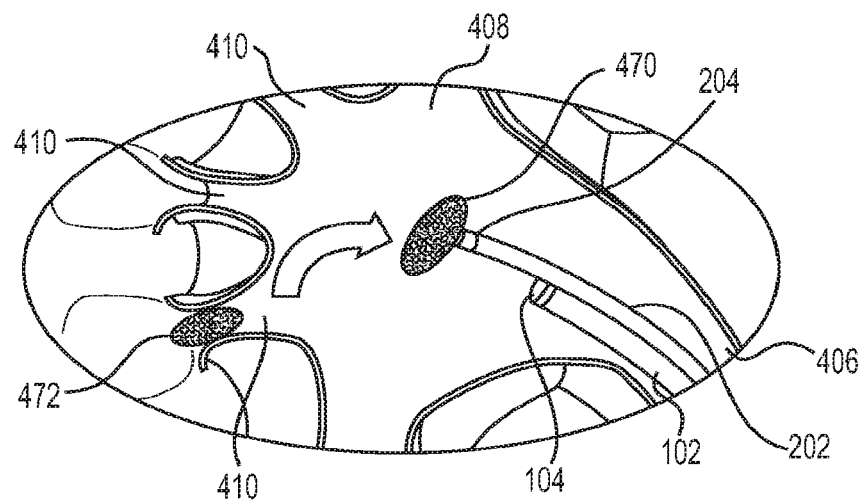
Figure 5C:
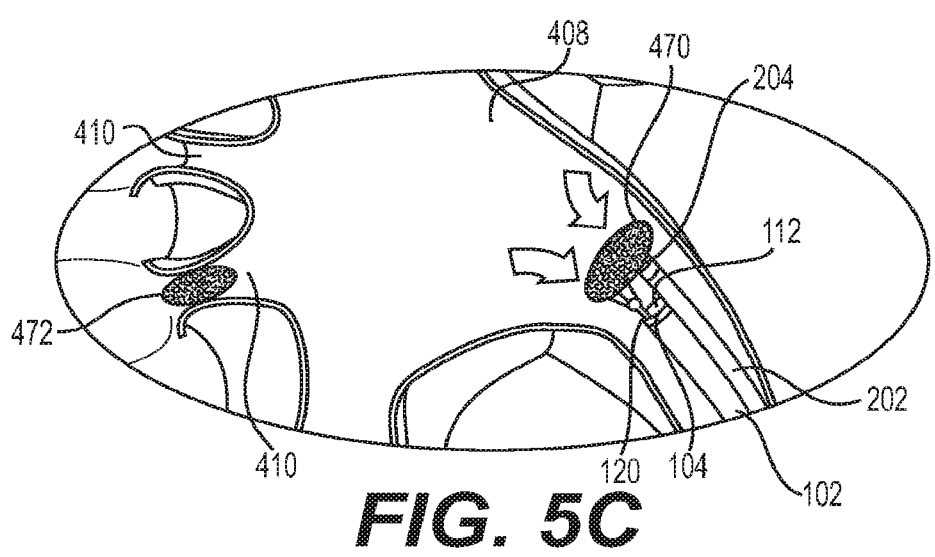

FIG. 5A-C illustrate an exemplary method of operation of medical device 100, including an enlarged view of upper ureter 406 and lower calyx 410 of kidney 408. Kidney stones 470 and 472 are located in lower calyx 410. As previously mentioned, the space within calyx 410 of kidney 408 is often more limited than the space within the ureter 406.

An operator (e.g., a doctor or other medical professional) may connect elongate member 202 and tube 102 by sliding their respective distal ends through a proximal opening of sleeve 302. In some examples, medical device 100 may be pre-assembled and this step may omitted. In some examples, one or both of tube 102 and elongate member 202 may be separately or simultaneously inserted into patient's urethra, through the urinary bladder, and into ureter 406. In examples in which elongate member 202 is used as a guidewire, distal end 204 of elongate member 202 may be inserted into a patient's urethra, through the urinary bladder, and into ureter 406. In some examples, once distal end 204 of elongate member 202 is positioned within the upper ureter, an operator may initiate the introduction of fluid into kidney 408 through lumen 214 of elongate member 202. For example, a fluid source (e.g., fluid source 280 of FIG. 1) may be fluidly connected to first end 244 of elongate member 202 and fluid may be transmitted through first end 244, through lumen 214 of elongate member 202, to distal end 204 of elongate member 202, and into the kidney 408. In some examples, the fluid may be radiopaque dye. As shown in FIG. 5A, dye 550 may enter the ureter 406 and/or kidney 408 (depending on the location of distal end 204 of elongate member 202) and may disperse throughout kidney 408 and/or lower calyx 410. This may allow the operator to determine the location of any kidney stones within the kidney. The introduction of any fluid (e.g., not limited to radiopaque) into the kidney may at least partially inflate the kidney, thus providing additional space to perform the desired procedure. Further, the introduction of fluid as an initial step may ensure that the pressure within the kidney remains at a sufficient level, e.g., the kidney will not collapse, once suction is applied to the kidney through lumen 214 of elongate member 202 (as described in further detail below). It should be noted that in some examples, fluid is not introduced through lumen 214 of elongate member 202, and once disposed with the patient's body, an operator may proceed to the next step, e.g., locating and securing a kidney stone.

Elongate member 202 may be extended distally into kidney 408, so that the distal opening of lumen 214 is proximate to kidney stone 470. At this point, elongate member 202 is in a retrieval position, e.g., distal end 204 of the elongate member 202 is positioned distal of distal end 104 of tube 102. An operator may initiate a vacuum source, e.g., by selecting input device 230 of FIG. 4, to apply suction through lumen 214 to distal end 204 of elongate member 202. Suction into lumen 214 of elongate member 202 may pull the stone toward a distal opening of elongate member 202 until the stone contacts and forms a seal with the distal opening of elongate member 202. The formed seal may secure the kidney stone to the distal opening of the elongate member 202. As shown in FIG. 5B, with the stone secured to elongate member 202, elongate member 202 may be retracted or pulled proximally toward ureter 406 and/or distal end 104 of tube 102 until the elongate member is in the operating position, e.g., secured stone 470 is proximate a distal opening of tube 102. At any time between the insertion of elongate member 202 into the patient and the above step of securing the stone proximate the distal opening of tube 102, tube 102 may track elongate member 202 like a guidewire, so that distal end 104 is positioned within ureter 406. FIG. 5C illustrates an operating position of elongate member 202 in which distal end 204 of elongate member 202 is closer to distal end 104 of tube 102 than in the retrieval position.

As shown in FIG. 5C, once the laser fiber 120 is in a sufficient position to aim for secured kidney stone 470, the operator may initiate the laser to break up kidney stone 470. Laser fiber 120 may be introduced into a patient through lumen 112 of tube 102. Laser fiber 120 may be connected to and/or controlled by laser control 130. (It should be noted that the stone may be broken into particles in any way known in the art, including the application of ultrasound and/or sound waves on the stone.) Once stone 470 is broken into particles that are smaller than the cross-sectional area of the distal opening of elongate member 202, the seal may be broken and/or particles may be suctioned into lumen 214 of elongate member 202. These particles may be vacuumed through elongate member 202 and out of the patient's body. The stone particles are suctioned out from lumen 214 of elongate member 202 along with the used saline fluid and collect in the chamber outside the patient body through the saline outlet pathway.

The application of suction through lumen 214 of elongate member 202 may improve the ability to break kidney stones by creating an anti-retropulsion effect. By applying suction through lumen 214, a kidney stone may be pulled toward laser fiber 120, thus countering the effect of the laser energy pushing the kidney stone away. This configuration thus assists in generating the smaller stone fragments by pulling the stones into the reach of laser fiber 120.

Once the operator determines a sufficient amount of the resulting particles of stone 470 have been removed from the patient's body or does not want to continue for other reasons, the laser process and/or application of suction may be stopped. At any point, an operator may additionally choose to move the device within the patient. For example, an operator may choose repeat the process. In FIG. 5C, elongate member 202 has secured a first kidney stone 470, but a second kidney stone 472 remains within lower calyx 410. Once kidney stone 470 has been removed from the patient's body, the operator may move distal end 204 of elongate member 202 to a retrieval position and position its distal opening proximate to kidney stone 472. The above process may then be repeated for securing, moving, and breaking up stone 472. An operator may reposition any element of the medical device and/or repeat any of the above described steps any number of times. Once an operator determines no more kidney stones can and/or should be broken apart and/or no more stone fragments/dust can and/or should be removed, medical device 100 may be removed from the patient's body.

Figure 6:
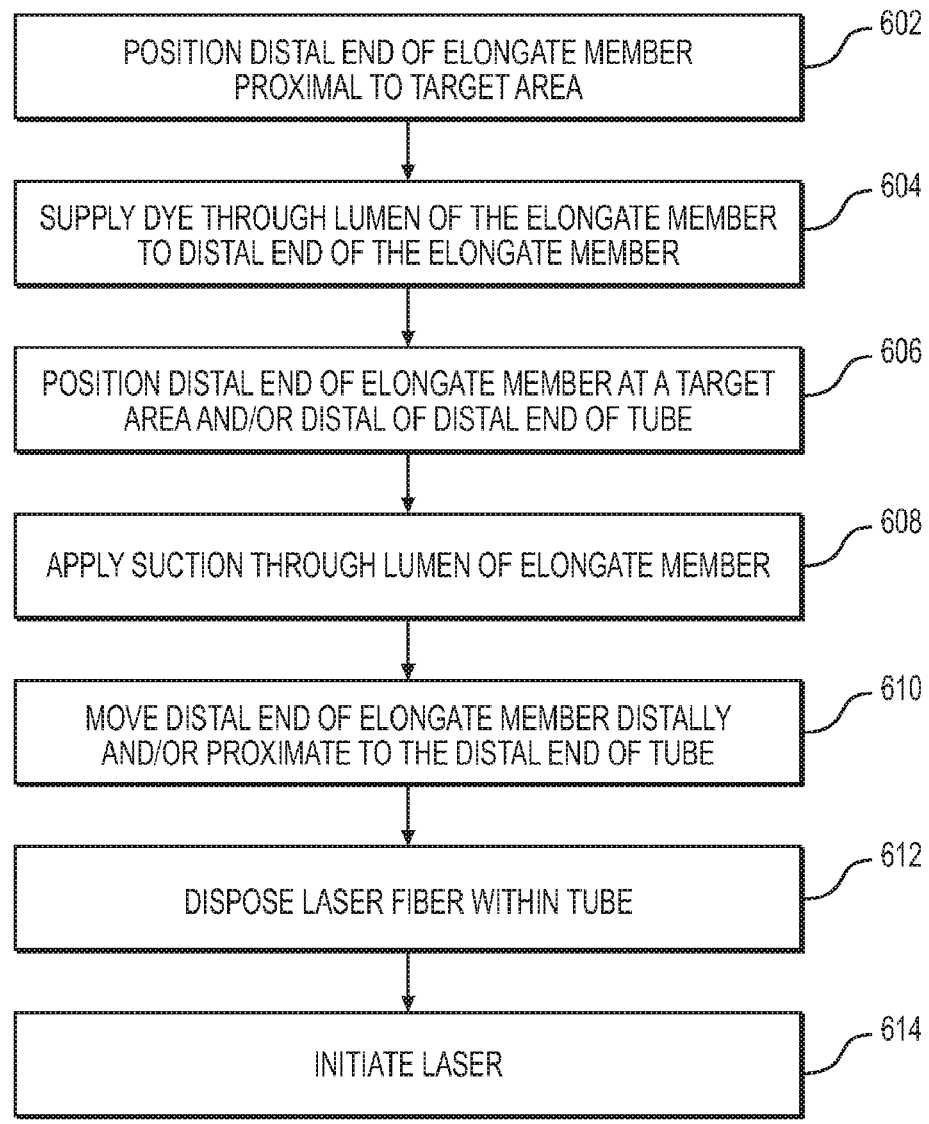
FIG. 6 is a block diagram of an exemplary method of using the medical devices disclosed herein.

FIG. 6 illustrates an exemplary method of use of a medical device for removal of stone fragments/dust. For purposes of discussion, method 600 will be described using medical device 100 of FIG. 1 and the urinary system of FIGS. 5A-C, as described above, but method 600 is not intended to be limited thereto. As shown in FIG. 6, method 600 includes steps 602, 604, 606, 608, 610, 612, and 614. However, it should be noted that method 600 may include more or fewer steps as desired for a particular implementation and the order of the steps may be varied.

Method 600 may commence after elongate member 202 and/or tube 102 of medical device 100 have been inserted into a patient's body. In step 602, distal end 204 of elongate member 202 may be positioned proximal of a target area (e.g., kidney 408 and/or lower calyx 410). In step 604, as illustrated in FIG. 5A, dye (e.g., dye 550) may be supplied through a lumen (e.g., lumen 214) of the elongate member (e.g., elongate member 202) to the distal end (e.g., distal end 204) of the elongate member. In step 606, distal end 204 of elongate member 202 may be positioned at the target area (e.g., kidney 408 and/or lower calyx 410) and/or distal of distal end 104 of tube 102. Once distal end 204 of elongate member 202 is proximate an object (e.g., kidney stone 470), method 600 may proceed to step 608 and suction may be applied through lumen 214 of elongate member 202. An operator may apply suction to lumen 214 of elongate member 202 by, for example, initiating vacuum source 250 of FIG. 1. The application of suction may move the object to the distal opening of lumen 214 and the object (e.g., kidney stone 470) may form a seal with distal end 204 of elongate member 202. In some examples, distal end 204 of elongate member 202 may be repositioned in order to capture the object with the applied suction. Once a seal is formed, method 600 may proceed to step 610. In step 610, distal end 204 of elongate member 202 may be moved distally and/or proximate to distal end 104 of tube 102, as shown in FIG. 5B. Moving distal end 204 of elongate member 202 may also move the object (e.g., kidney stone 470) distally and/or proximate to distal end 104 of tube 102. In step 612, once the object is proximate to distal end 104 of tube 102, a laser fiber may be disposed within the tube. For example, laser fiber 120 may extend through lumen 112 to distal end 104 of tube 102 and may aim at kidney stone 470. In step 614, the laser may be initiated. For example, an operator may initiate the laser through laser control 130 and/or handle portion 110 of FIG. 1.

The many features of the disclosure are apparent from the detailed specification, and thus, it is intended by the appended claims to cover all such features of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
a delivery device including a tube having a distal end, a proximal end, and a lumen extending between the proximal end and the distal end; and
a member having a distal end, a proximal end, and a lumen extending between the proximal end and the distal end, wherein the lumen is configured to apply suction through the distal end of the member, wherein at least a distal portion of the member is D-shaped with a flat side and a rounded side extending from opposing ends of the flat side;
wherein at least one of the tube or the member is axially movable relative to the other of the tube or the member;
wherein at least a portion of a circumferential exterior of the tube abuts a portion of the flat side of the member; and
wherein an outer portion of the tube includes a flat engaging surface that is complementary to the flat side of the distal portion of the member.

2. The medical device of claim 1, wherein the delivery device is one of a ureteroscope, a sheath, a catheter, or an endoscope.

3. The medical device of claim 1, wherein the distal end of the tube includes an illumination device and an imaging device, and wherein the medical device further comprises a laser fiber connected to the tube.

4. The medical device of claim 1, wherein the member is movable to extend distally beyond the tube to apply suction to an object at a first position and retract proximally to bring the object to a second position closer to the distal end of the tube.

5. The medical device of claim 1 wherein the tube includes a partially circular portion extended from opposite sides of the flat engaging surface.

6. The medical device of claim 1, further comprising a sleeve, wherein the delivery device and the member are adjacent to each other at least partially within the sleeve.

7. A medical device, comprising:
a tube having a distal end, a proximal end, and a lumen extending between the proximal end and the distal end; and
a member having a distal end, a proximal end, and a lumen extending between the proximal end and the distal end, wherein the lumen is configured to apply suction through the distal end of the member, wherein at least a distal portion of the member is D-shaped with a flat side and a rounded side extending from opposing ends of the flat side,
wherein at least a portion of a circumferential exterior of the tube includes a flat engaging surface that is complementary to and abuts a portion of the flat side of the member,
wherein the tube includes a partially circular portion extended from opposite sides of the flat engaging surface, and
wherein at least one of the tube or the member is axially movable relative to the other of the tube or the member.

8. The medical device of claim 7, further comprising a sleeve, wherein the tube and the member are adjacent to each other at least partially within the sleeve.

9. The medical device of claim 8, wherein the distal end of the tube includes an illumination device and an imaging device, and wherein the medical device further comprises a laser fiber connected to the tube.

10. The medical device of claim 7, wherein the member is movable relative to the tube to extend distally beyond the tube to apply suction to an object at a first position and retract proximally to bring the object to a second position closer to the distal end of the tube.

11. The medical device of claim 10, further comprising a laser element within the lumen of the tube, wherein the laser element is longitudinally moveable within the lumen of the tube to extend distally beyond the distal end of the tube.

12. The medical device of claim 7, wherein the distal end of the member includes a reinforced section.

13. The medical device of claim 7, wherein the medical device includes a handle, wherein the member is operably coupled to a control system, wherein the tube is operably coupled to the handle, wherein the member is configured to be coupled to a suction source, and wherein the member is movable relative to the tube to extend distally beyond the tube to apply suction to an object at a first position and retract proximally to bring the object to a second position closer to a distal end of the tube.

14. A medical device, comprising:
a delivery device including a tube having a distal end, a proximal end, and a lumen extending between the proximal end and the distal end; and
a member having a distal end, a proximal end, and a lumen extending between the proximal end and the distal end, wherein the lumen is configured to apply suction through the distal end of the member, wherein at least a distal portion of the member is D-shaped with a flat side and a rounded side extending from opposing ends of the flat side;
wherein the member is axially movable relative to the tube such that the member is extendable distally of the tube,
wherein at least a portion of a circumferential exterior of the tube abuts a portion of the flat side of the member,
wherein an outer portion of the tube includes a flat engaging surface that is complementary to the flat side of the distal portion of the member, and
wherein another outer portion of the tube includes a rounded portion extending from opposite sides of the flat engaging surface.

15. The medical device of claim 14, wherein the delivery device is one of a ureteroscope, a sheath, a catheter, or an endoscope.

16. The medical device of claim 14, wherein the distal end of the tube includes an illumination device and an imaging device, and wherein the medical device further comprises a laser fiber connected to the tube.

17. The medical device of claim 14, wherein the member is movable to extend distally beyond the tube to apply suction to an object at a first position and retract proximally to bring the object to a second position closer to the distal end of the tube.

18. The medical device of claim 14, wherein the tube includes a partially circular portion extended from opposite sides of the flat engaging surface.

19. The medical device of claim 14, further comprising a sleeve, wherein the delivery device and the member are adjacent to each other at least partially within the sleeve.

20. The medical device of claim 19, wherein the medical device includes a handle, wherein the member is operably coupled to a control system, wherein the tube is operably coupled to the handle, wherein the member is configured to be coupled to a suction source, and wherein the member is movable relative to the tube to extend distally beyond the tube to apply suction to an object at a first position and retract proximally to bring the object to a second position closer to a distal end of the tube.

* * * * *